(12) United States Patent
Lietzke et al.

(10) Patent No.: US 10,302,551 B2
(45) Date of Patent: May 28, 2019

(54) INTELLIGENT SENSOR POINTING FOR REMOTE SENSING APPLICATIONS

(71) Applicant: Harris Corporation, Melbourne, FL (US)

(72) Inventors: Christopher E. Lietzke, Fort Wayne, IN (US); John R. Holder, Fort Wayne, IN (US); Anthony Wayne New, Fort Wayne, IN (US)

(73) Assignee: Harris Corporation, Melbourne, FL (US)

( * ) Notice: Subject to any disclaimer, the term of this patent is extended or adjusted under 35 U.S.C. 154(b) by 0 days.

(21) Appl. No.: 15/683,442

(22) Filed: Aug. 22, 2017

(65) Prior Publication Data

US 2019/0064055 A1  Feb. 28, 2019

(51) Int. Cl.
*G01N 21/01* (2006.01)

(52) U.S. Cl.
CPC ..... *G01N 21/01* (2013.01); *G01N 2021/0181* (2013.01)

(58) Field of Classification Search
CPC ....... G01J 5/007; G01J 5/505; G01B 11/0608; G01C 11/06; G01C 11/04; G01W 1/10; G06K 9/0063; G06K 9/6284; G06K 9/4647; G06K 9/4652; G08G 5/0091; B64D 47/08

USPC ......................... 356/437, 336, 434
See application file for complete search history.

(56) References Cited

U.S. PATENT DOCUMENTS

| 8,594,375 | B1* | 11/2013 | Padwick | G06K 9/0063 |
| | | | | 382/103 |
| 8,614,794 | B2 | 12/2013 | Smith et al. | |
| 2005/0114026 | A1* | 5/2005 | Boright | G01W 1/00 |
| | | | | 702/3 |
| 2013/0266221 | A1* | 10/2013 | Kaneko | G06T 5/00 |
| | | | | 382/168 |
| 2016/0283774 | A1* | 9/2016 | Buchanan | G06K 9/0063 |

* cited by examiner

*Primary Examiner* — Isiaka O Akanbi
(74) *Attorney, Agent, or Firm* — Edell, Shapiro & Finnan, LLC

(57) ABSTRACT

A technique for measuring atmospheric conditions includes: at a computing device, receiving, from an imager, image data representing an image of an atmospheric region; creating a cloud mask from the image data, the cloud mask including a cloud area corresponding a first area in the image that is cloud covered and a non-cloud area corresponding a second area in the image that is substantially without cloud cover; determining a measurement location in the non-cloud area that is spaced apart from a boundary of the cloud area and from edges of the cloud mask; steering a line of sight of a sensor to correspond to the measurement location; and measuring an atmospheric condition with the sensor at the measurement location within the non-cloud area.

20 Claims, 9 Drawing Sheets

INTELLIGENT SENSOR POINTING FOR REMOTE SENSING APPLICATIONS

TECHNICAL FIELD

The present disclosure is directed to remote sensing systems and, in particular, to a system and method for intelligently pointing a sensor to a desired sensing location.

BACKGROUND

To accurately measure atmospheric conditions such as greenhouse gas concentrations, sensors must be pointed toward cloud-free "open sky" areas. For example, a downward looking sensor that passively detects spectral content associated with greenhouse gases can be mounted on an Earth-orbiting satellite. Using a mirror system or the like, the line of sight of the sensor can be steered over a range of angles so that measurements can be taken in a number of different directions within a region of the Earth's atmosphere.

Conventionally, the process of taking sensor measurements in several directions within a region has been performed without knowing whether clouds obscure the sensor's field of view (FOV) in any of the directions. Only after later evaluating a contemporaneously generated visual image of the region can it be determined whether the field of view of each of the measurements was in cloud-free areas and therefore usable. FIG. 1 shows a conventional method of scanning a region to detect greenhouse gas concentrations. Within the region, a sensor is sequentially pointed to twelve angular locations (e.g., at regular intervals in a two-dimensional raster scan), labeled 1 through 12, to collect information. At each location, the sensor is configured to detect greenhouse gas concentrations in a FOV area, represented by the circles in FIG. 1. As shown in FIG. 1, out of the twelve locations, the sensor is able to accurately sense greenhouse gas concentration only at location 10 (shown in dashed lines), since the FOV area at location 10 is free of clouds. As a result, only one out of twelve measurements collected by the sensor can be used in this example. Because the sensor system is unaware of the presence or location of cloud cover, the system cannot steer the sensor angle to specific locations to take advantage of significant open-sky areas that may exist in the region. Once the entire region in FIG. 1 has been scanned by the sensor, the sensor is moved to the next region to repeat the scanning process. Despite the considerable time required to sequentially scan a number of regions of interest, many of the measurements may not be useable due to cloud cover, and the success rate of collecting useful data is low.

To improve the success rate, a smaller FOV may be used. And to reduce the time for scanning, a plurality of sensors can be employed to scan a region. FIG. 2 shows another conventional method of scanning using eight sensors disposed in a row. In operation, the eight sensors produce eight FOVs in a row, represented by eight circles in one row. The row of FOVs are moved in a direction represented by an arrow in FIG. 2 to scan the region. Because eight sensors are employed to scan the region, the time required to scan the entire region is reduced. Further, because a smaller FOV is used, more areas (in the broken-line circles) not covered with cloud can be used to detect gashouse gas concentrations, improving the number of useful measurements within a region. However, the use of smaller FOV results in lower signal to noise ratios, and hence lower-quality measurements, and the method still collects data that cannot be used for the purpose of detecting gashouse gas concentrations.

SUMMARY

Described herein are techniques for intelligently pointing a sensor to remotely measure atmospheric conditions by identifying substantially cloud-free regions where measurements can successfully be taken. Using image data representing an image of an atmospheric region, a cloud mask is created. The cloud mask includes a cloud area corresponding to a first area in the image that is cloud covered and a non-cloud area corresponding to a second area in the image that is substantially without cloud cover. A desired measurement location in the non-cloud area is identified that is spaced apart from a boundary of the cloud area and from edges of the cloud mask, and the line of sight of a sensor is steered to correspond to the measurement location. An atmospheric condition can then be measured with the sensor at the measurement location within the non-cloud area. These techniques may be embodied as a method, a system, an apparatus, and instructions in a computer-readable storage media to perform the method.

In one aspect, hue (H), saturation (S), and value (V) data from the image data is used to determine whether each pixel is in the cloud area or the non-cloud area of the cloud mask. For example, a pixel can be determined to be in the cloud area if the saturation (S) value of the pixel is greater than a first threshold value and the V value of the pixel is less than a second threshold value. According to another example, a pixel can be determined to be in the cloud area if an absolute value of a difference between the red (R) value and the green (G) value of the pixel is less than or equal to a first threshold value and a difference between the blue (B) value and an average of the R value and the G value is greater than a second threshold valve. According to another example, the minimum of the red, green, and blue values of a pixel is identified, and the pixel is determined to be in the cloud area of the cloud mask if the minimum is greater than a first threshold value, or the pixel is determined to be in the non-cloud area of the cloud mask if the minimum is below a second threshold value.

In another aspect, determining the measurement location includes convolving the cloud mask with a sensor field of view to generate a first convolved mask, and convolving the first convolved mask with the sensor field of view to generate a second convolved mask. The measurement location can be determined by finding a minimum value in the second convolved mask.

BRIEF DESCRIPTION OF THE DRAWINGS

Like reference numerals have been used to identify like elements throughout this disclosure.

DETAILED DESCRIPTION

Presented herein are techniques for intelligently pointing a sensor to a desired location to conduct a sensing mission, such as detecting greenhouse gas concentrations, weather detection, weaponry detection or, generally, any detection/sensing conducted from space (from an Earth-orbiting satellite) or aircraft. In particular, a detection or sensing from space or aircraft may be obstructed by the presence of clouds at the detection area. Techniques disclosed herein can detect areas that are not covered with clouds or covered with fewer clouds and intelligently point the sensor to those non-cloud or less-cloud areas to conduct the sensing mission.

Figure 3:
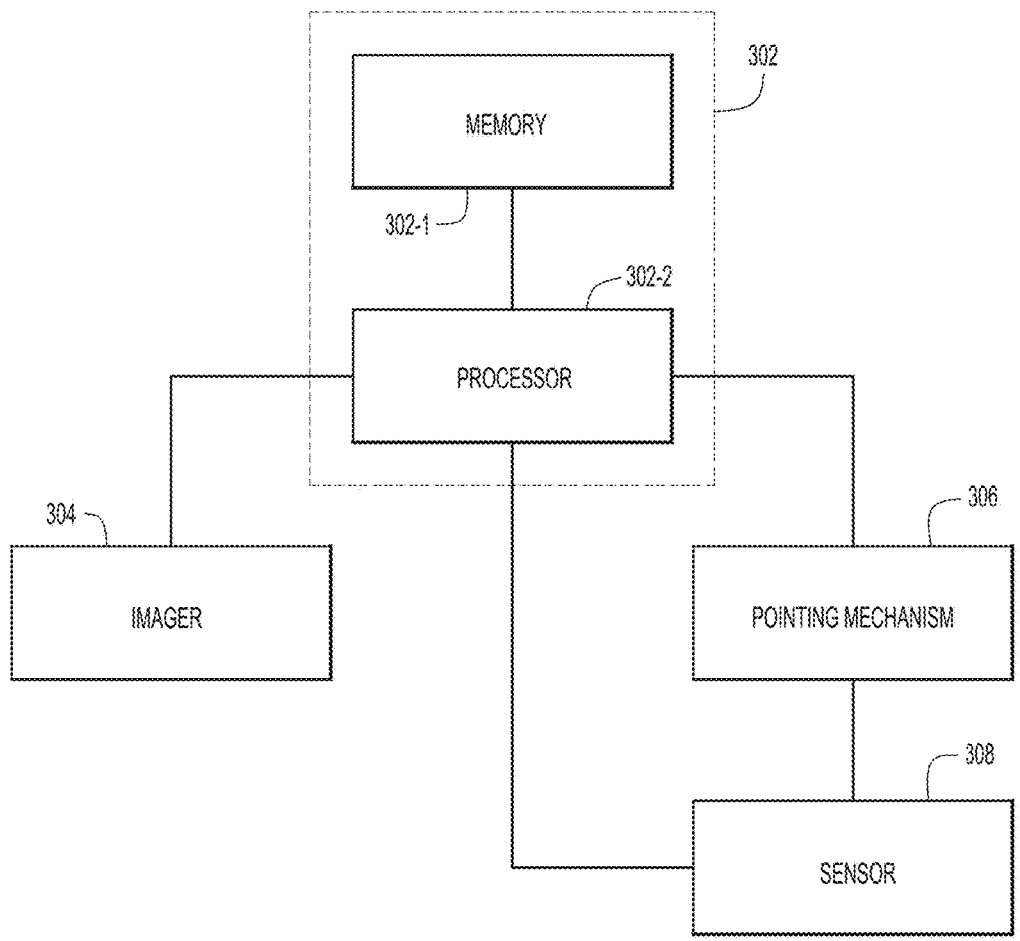
FIG. 3 is a high-level block diagram of an example sensing system for performing remote sensing of an atmospheric condition.

FIG. 3 is a block diagram depicting a system 300 for conducting an intelligent sensing mission, according to an example embodiment. The system 300 includes a computing apparatus 302, an imager 304, a pointing/steering mechanism 306, and one or more sensors 308. The computer apparatus 302 includes a memory 302-1 and a processor 302-2. The processor 302-2 may be a microprocessor or microcontroller (or multiple instances of such components) that is configured to execute program logic instructions (i.e., software) for carrying out various operations and tasks described herein. For example, the processor 302-2 is configured to execute instructions for intelligent pointing logic stored in the memory 302-1 to identify a non-cloud or less-cloud area and control the pointing mechanism 306 and sensor 308 to conduct sensing missions at the identified areas. Further descriptions of the operations performed by the processor 302-2 when executing instructions stored in the memory 302-1 are provided below.

The memory 302-1 may include read only memory (ROM), random access memory (RAM), magnetic disk storage media devices, optical storage media devices, flash memory devices, electrical, optical or other physical/tangible memory storage devices.

The functions of the processor 302-2 may be implemented by logic encoded in one or more tangible (non-transitory) computer-readable storage media (e.g., embedded logic such as an application specific integrated circuit, digital signal processor instructions, software that is executed by a processor, etc.), wherein the memory 302-1 stores data, such as images provided by imager 304, used for the operations described herein and stores software or processor executable instructions that are executed to carry out the operations described herein.

The intelligent pointing logic may take any of a variety of forms, so as to be encoded in one or more tangible/non-transitory computer readable memory media or storage device for execution, such as fixed logic or programmable logic (e.g., software/computer instructions executed by a processor), and the processor 302-2 may be an application specific integrated circuit (ASIC) that comprises fixed digital logic, or a combination thereof.

For example, the processor 302-2 may be embodied by digital logic gates in a fixed or programmable digital logic integrated circuit, which digital logic gates are configured to perform the intelligent pointing logic. In general, the intelligent pointing logic may be embodied in one or more computer-readable storage media encoded with software comprising computer executable instructions and when the software is executed operable to perform the operations described herein.

The imager 304 is coupled to the computing apparatus 302 and configured to take images from overhead and transmit image data of the images to computing apparatus 302. In some embodiments, before transmitting image data to the computing apparatus, the imager 304 may be configured to aggregate a group of adjacent pixels in an image into aggregated pixels so as to generate an aggregated image. The images taken by the imager 304 may include visible and/or infrared image data. Visible image data may include colored pixel data and/or grayscale pixel data. In one embodiment, the imager 304 may be a Bayer image camera or digital video recorder that produces an image including red (R), green (G), and blue (B) pixel data.

The pointing mechanism 306 is coupled to the processor 302-2 and configured to receive instructions from the processor 302-2 for pointing the sensor 308 to a desired location. In some embodiments, the pointing mechanism 306 may include a mirror set or other optical elements and mechanical components that direct the sensor to receive light signals.

The sensor 308 is coupled to the pointing mechanism 306 and the processor 302-2. The sensor 308 is configured to collect signals for sensing missions. In some embodiments, the sensor 308 may include a light detector that collects light signals for sensing missions. For example, the sensor 308 may passively receive electromagnetic energy in the visible, infrared, or ultraviolet spectrum and generate spectral data indicating the presence of certain elements, compounds, or substances within the field of view of the sensor based on the spectral signature of the measurement at certain wavelengths. Depending on the needs of the sensing mission, the sensor 308 may include other types of detectors to fulfill the requirements for the sensing mission. While the disclosure focuses on the example of detecting greenhouse gas concentrations for illustrative purposes, it will be appreciated that the invention is not limited to this particular application or type of sensor, and the techniques described herein are applicable to other types of sensors and applications where measurements may be impacted by the presence or absence of atmospheric clouds (e.g., satellite ground mapping).

Figure 4A:
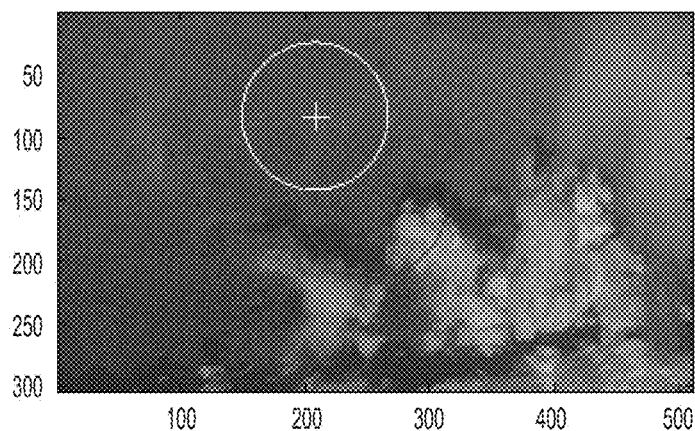
FIG. 4A is an image of an atmospheric region experiencing partial cloud cover.

At the outset, the system 300 may be mounted on a satellite in a look-down configuration or carried by an aircraft to conduct a sensing mission. According to another option, the sensor and pointing system can be terrestrial-based (e.g., stationary or vehicle-mounted) in an upward-looking configuration. In the case of a satellite or airborne installation, once situated, the processor 302-2 is configured to instruct the imager 304 to take a downward-looking "bird's eye view" image over the region beneath the imager 304. In some embodiments, the images taken by the imager are color images, such as Bayer images, that include at least RGB pixel data. In other embodiments, the images taken by the imager 304 may include image data in infrared spectrum or in grayscale. In a non-limiting example, an image may comprise a two-dimensional array of 608×1024 pixels, and a pixel may represent an area corresponding to 50 meters by 50 meters. An example image taken by an imager is shown in FIG. 4A.

Figure 4B:
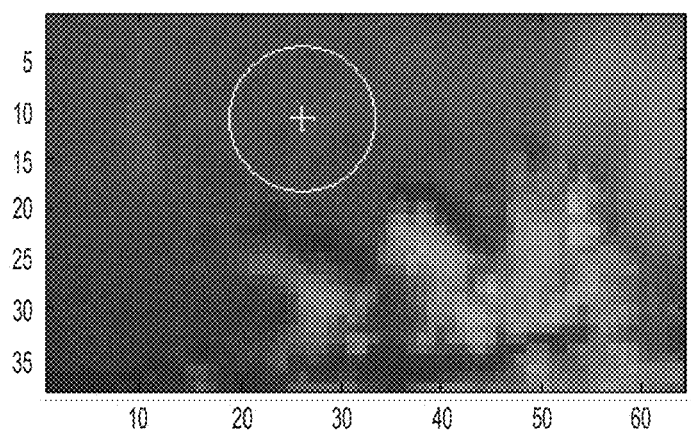
FIG. 4B is an aggregated image generated by aggregating pixels of the image shown in FIG. 4A, according to an example embodiment.

The imager 304 then transmits the image data to the processor 302-2. In some embodiments, before the processor 302-2 begins to identify a desirable location in the image to point the senor 308 to that location, the image data of the image may be aggregated. For example, the imager 304 may aggregate the pixels in the image before transmitting image data to the processor 302-2. The imager 304 may aggregate a group of adjacent pixels to form aggregated pixels so as to generate an aggregated image from the image. In a non-limiting example, an image having 608×1024 pixels may be transformed to an aggregated image having 38×64 pixels. In some embodiments, the processor 302-2 may be configured to perform the aggregation. FIG. 4B shows an example aggregated image based on the image shown in FIG. 4A. Such an aggregation process may be useful where the processing capabilities of the processor are insufficient to perform the necessary operations on the original image to meet operational requirements (e.g., in real time or near real time).

Figure 4C:
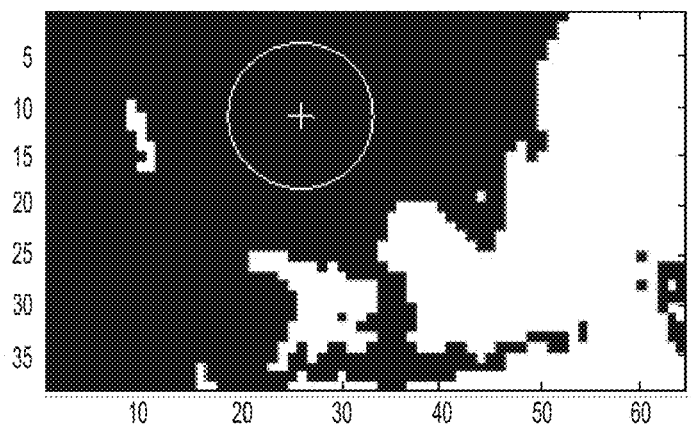
FIG. 4C is a cloud mask generated using a cloud detection algorithm, according to an example embodiment.

After receiving the image data or aggregated image data, the processor 302-2 applies a cloud detection algorithm to the image data to create a cloud mask. The cloud mask includes a cloud area corresponding to an area in the image that is covered with clouds and a non-cloud area corresponding to another area in the image that is substantially without cloud cover. FIG. 4C shows an example cloud mask created from the aggregated image shown in FIG. 4B. In FIG. 4C, cloud areas are represented by white color while non-cloud areas are represented by black color. The details of the cloud detection algorithm will be explained in the description below. Using the cloud mask, the processor 302-2 is configured to determine a specific measurement location in a non-cloud area that is spaced apart from a boundary of the cloud area(s) and from edges of the cloud mask as a desired location for the sensor 308 to measure an atmospheric condition. As used herein and in the claims, the term "substantially without cloud cover" refers to a portion of the atmospheric region of interest, and correspondingly an area in the cloud mask, that is entirely cloud-free or else has sufficiently minimal cloud cover so as to fall below a threshold that establishes a maximum level of cloud presence that can be tolerated to make valid, useful measurements of an atmospheric condition of interest. Thus, the threshold for what constitutes "substantially without cloud cover" can be relative to the operational requirements for obtaining a valid measurement of a particular atmospheric condition (e.g., the concentration of a specific substance). Once the processor 302-2 locates the desired location, it controls the pointing/steering mechanism 306 to steer the line of sight of the sensor 308 to correspond to the desired location within the non-cloud area and instructs the sensor to start measuring an atmospheric condition, e.g., a passively received electromagnetic signal that indicates the concentration of one or more greenhouse gases.

To generate a cloud mask for identifying a desired location for a sensing mission, the processor 302-2 applies a cloud detection algorithm to image data collected by the imager 304. According to one implementation, in applying the cloud detection algorithm, the processor 302-2 converts red (R), green (G), and blue (B) (RGB) pixel data of the image data into hue (H), saturation (S), and value (V) data. The processor 302-2 then determines that a pixel is in the cloud area if an S value of the pixel is greater than a first threshold value and a V value of the pixel is less than a second threshold value.

According to another implementation, the processor 302-2 determines that a pixel is in the cloud area if an absolute value of a difference between an R value and a G value of the pixel is less than or equal to a third threshold value and a difference between a B value and an average of the R value and the G value is greater than a fourth threshold value.

In yet another implementation, the processor 302-2 determines a minimum of an R value, a G value, and a B value of a pixel, and determines that the pixel is in the cloud area if the minimum is greater than a fifth threshold value or that the pixel is in the non-cloud area if the minimum is less than a sixth threshold value. Where both thresholds are employed, the sixth threshold value is greater than the fifth threshold value. The various tests described in the aforementioned implementations can be employed individually or in various combinations which each other to determine whether a pixel is in the cloud area or the non-cloud area in order to construct the cloud mask. It will be appreciated that other tests or combinations of tests are possible for determining whether a pixel is in the cloud area or the non-cloud area. Further, the various thresholds in the aforementioned tests can be adjusted according to the maximum level of cloud presence that is tolerable for measuring a particular atmospheric condition.

In some embodiments, the threshold values employed in the cloud detection algorithm may be configurable and uploaded to the computing apparatus 302 through wired or wireless connection, and saved in the memory 302-1. A cloud mask can be created after each of the pixels of the image is examined by the cloud detection algorithm. For example, a pixel in a non-cloud area can be represented by zero (e.g., a black pixel) and a pixel in a cloud area can be represented by one (e.g., a white pixel) in a cloud mask, as shown in FIG. 4C.

Figure 4D:
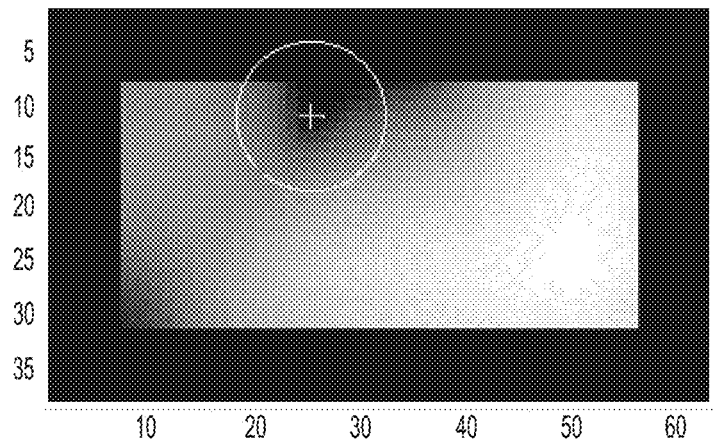
FIG. 4D is a convolved mask generated from the cloud mask shown in FIG. 4C, according to an example embodiment.

To determine a desired measurement location for the sensor 308 to acquire signals, the processor 302-2 is configured to determine a location in the non-cloud area that is spaced apart from a boundary of the cloud area(s) and from edges of the cloud mask. In some embodiments, the processor 302-2 is configured to apply a cloud avoidance algorithm to the cloud mask to determine the desired measurement location. In applying the cloud avoidance algorithm to the cloud mask, the processor 302-2 is configured to convolve the cloud mask with a FOV of the sensor 308 to generate a first convolved mask and convolve first convolved mask with the FOV to generate a second convolved mask. A convolved mask is shown in FIG. 4D. Thereafter, the processor 302-2 is configured to find a minimum value in the second convolved mask, representing a desired measurement location for the sensor to measure an atmospheric condition. The desired location is employed as the center of the FOV of the sensor 308 to measure signals in the region of the image. In the convolved mask shown in FIG. 4D, a FOV of a sensor is represented by a circle having a center represented by a cross mark at a location having the minimum value of the convolved mask.

In the illustrated embodiment, the convolution is performed by multiplying a matrix of the cloud mask with a matrix of the FOV mask where the value of the pixels within the FOV is assigned to be one (1) and, otherwise, the value of the pixels outside of the FOV is assigned to be zero (0). A value generated by the convolution is assigned to the pixel at the center of the FOV. To generate the first convolved mask, the FOV is configured to "scan" each of the pixels of the cloud mask. In other words, the center of the FOV mask is sequentially moved from one pixel location to the next, such that the FOV convolution value is determined at each pixel location. As each such location, the FOV mask comprises a "1" value at the pixel at which it is centered and at the pixels surrounding the center pixel out to a circular boundary corresponding the shape of the field of view of the sensor. In effect, the resulting convolution generates a two-dimensional array of values that indicate which locations (corresponding to pixels) would provide the most cloud-free field of view for the sensor if the line of sight of the sensor were to be steered to that angular direction (location). In this manner, the shape and size of the field of view of the sensor are accounted for relative to the cloud mask.

The second convolved mask can be generated using similar techniques used to generate the first convolved mask. More specifically, the FOV mask is sequentially moved from pixel to pixel across the first convolved mask, and at each pixel position, the convolution is performed by multiplying a matrix of the first convolved mask with a matrix of the FOV mask. Due to the integrating effect of the second convolution, the second convolved mask essentially generates minimum values at locations within the non-cloud area that are spaced apart from the boundaries of the cloud area and from the edges of the image. This has the effect of favoring locations that are more towards the center of a non-cloud area.

Figure 4E:
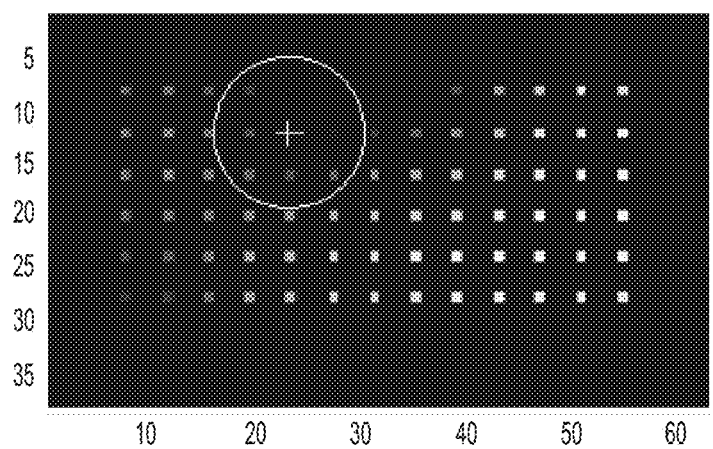
FIG. 4E is another convolved mask generated from the cloud mask shown in FIG. 4C, according to an example embodiment.

In some embodiments, the convolution may be performed at discrete pixels of the cloud mask, distanced from each other at a predetermined interval. For example, in a cloud mask having 38×64 pixels, the convolution can be performed at every other four pixels in the cloud mask to reduce the time required to calculate the desired location. An example second convolved mask generated using a number of discrete pixels of the cloud mask (FIG. 4C) is shown in FIG. 4E.

In some embodiments, to further improve sensing accuracy, the processor 302-2 is configured to compare the minimum value in the second convolved mask with a configurable threshold value and control the sensor to measure the atmospheric condition at the minimum-value location if the minimum value is less than the threshold value. The threshold value is configured to represent a maximum cloud coverage at a location that is acceptable for a sensor to collect useful data.

In the illustrated embodiments, the processor 302-2 can receive image data representing a region for a sensing mission. The processor 302-2 uses the image data to find a desired measurement location substantially without cloud cover, and instructs the pointing/steering mechanism 306 to steer the sensor 308 to measurement location (angular direction) to execute the sensing mission. The techniques presented herein improve detection success rate by pointing the sensor to a substantially cloud-free location so that the data collected from sensing is usable and accurate.

Figure 5:
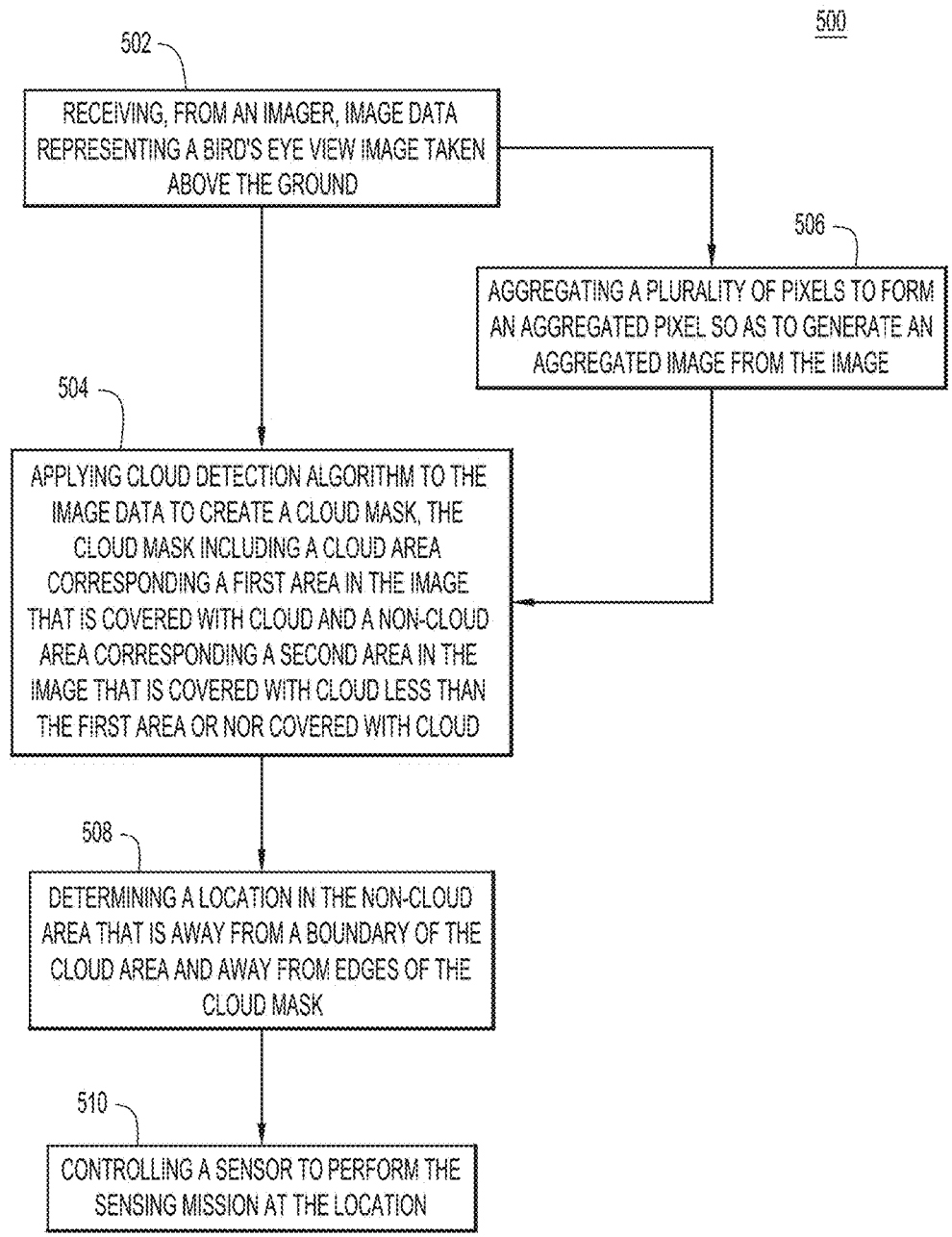
FIG. 5 is a flow chart illustrating a method for intelligently pointing a sensor to a measurement location for measuring an atmospheric condition, according to an example embodiment.

Referring now to FIG. 5 for a description of a method for intelligently pointing a sensor for measuring atmospheric conditions. FIG. 5 is a flow chart depicting a method 500 performed by a processor for executing a sensing mission, according to an example embodiment. The processor can be carried by a carrier, such as a vehicle, an airplane or a satellite. At 502, the processor receives, from an imager, image data representing an image of an atmospheric region. At 504, the processor applies a cloud detection algorithm to the image data and creates a cloud mask. The cloud mask includes a cloud area corresponding a first area in the image that is cloud covered and a non-cloud area corresponding a second area in the image that is substantially without cloud cover. In some embodiments, before applying the cloud detection algorithm to the image data, at 506 the image data of the image may be aggregated to reduce the amount of data for processing. In particular, the imager, which took the image, or the processor can aggregate a group of adjacent pixels of the image to form aggregated pixels so as to generate an aggregated image from the image. If the aggregation is performed by the imager, operation 506 takes place before operation 502. At 508, the processor determine a desired measurement location (correspond angular position of the sensors' line of sight) in the non-cloud area that is spaced apart from a boundary of the cloud area and from edges of the cloud mask. At 510, the processor causes a line of sight of a sensor to be steered to correspond to the measurement location. At 512, the processor causes the sensor to measure an atmospheric condition at the measurement location within the non-cloud area.

Figure 6:
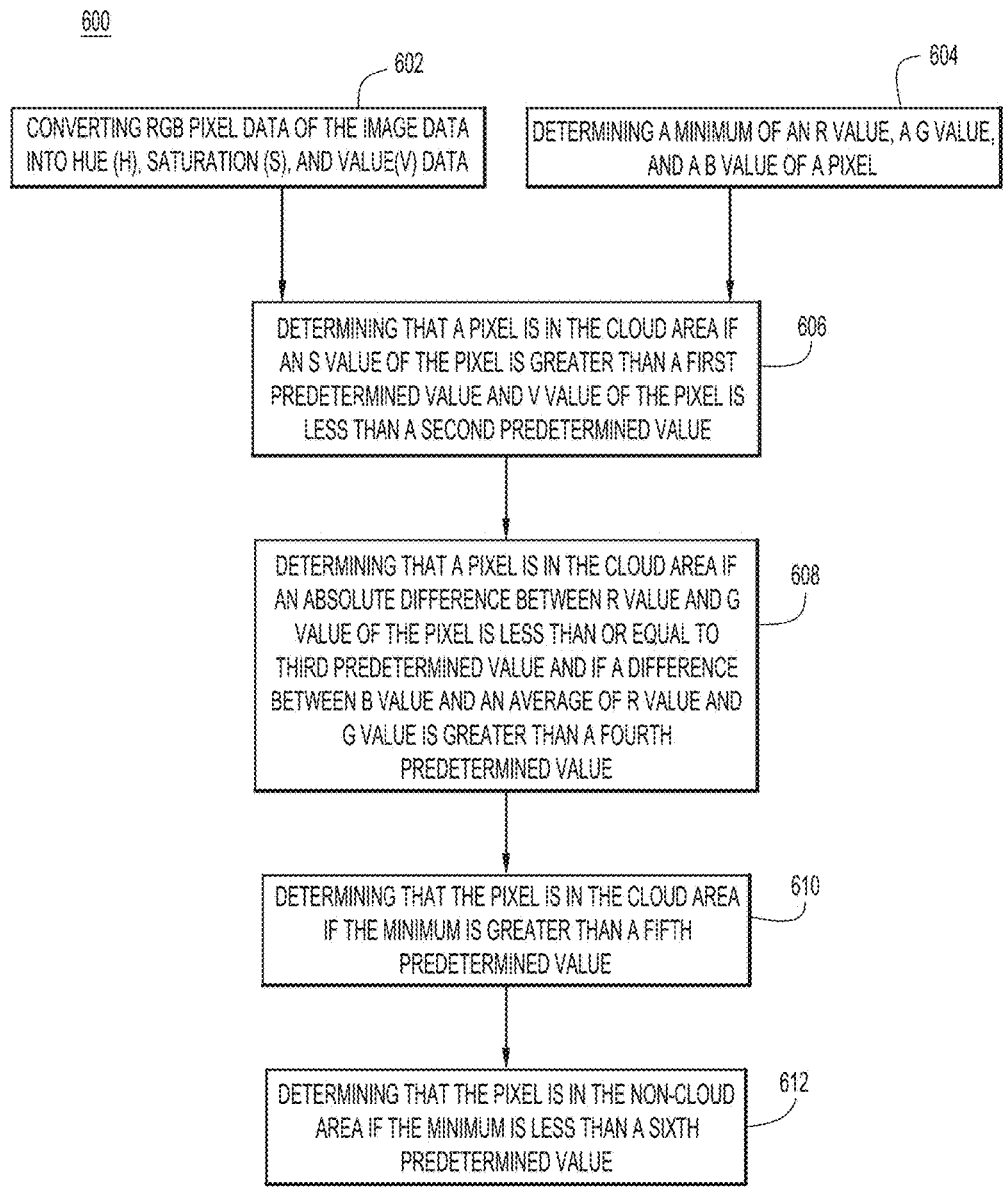
FIG. 6 is a flow chart illustrating a method for detecting clouds in an image, according to an example embodiment.

FIG. 6 is a flow chart depicting a method 600 for detecting a cloud area or cloud areas in an image performed by a processor, according to an example embodiment. For example, the method 600 may be embodied as cloud detection algorithm executable by the processor at operation 504 (FIG. 5). At 602, the processor receives image data including RGB pixel data and converts the RGB pixel data of the image data into HSV data. At 604, the processor determines a minimum (M) of an R value, a G value, and a B value of a pixel. In a non-limiting example, an S value can be defined as a maximum value of the RGB values, and a V value can be defined as a function of both the maximum and minimum values of the RGB values. For example, a V value can be defined as $V=255*(S-M)/S$. At 606, the processor determines that a pixel is in the cloud area if an S value of the pixel is greater than a first threshold value and a V value of the pixel is less than a second threshold value. At 608, the processor determines that a pixel is in the cloud area if an absolute value of a difference between an R value and a G value of the pixel is less than or equal to a third threshold value and if a difference between a B value and an average of the R value and the G value is greater than a fourth threshold value. At 610, the processor determines that a pixel is in the cloud area if the minimum of its RGB values is greater than a fifth threshold value. At 612, the processor determines that a pixel is in the non-cloud area if the minimum of its RGB values is less than a sixth threshold value. Operations 606-612 are employed to determine whether a pixel is in a cloud area or a non-cloud area, which is not covered by clouds or is substantially without cloud cover. In one embodiment, a pixel in an image or aggregated image may be examined by any one or more of operations 606-612.

Figure 7:
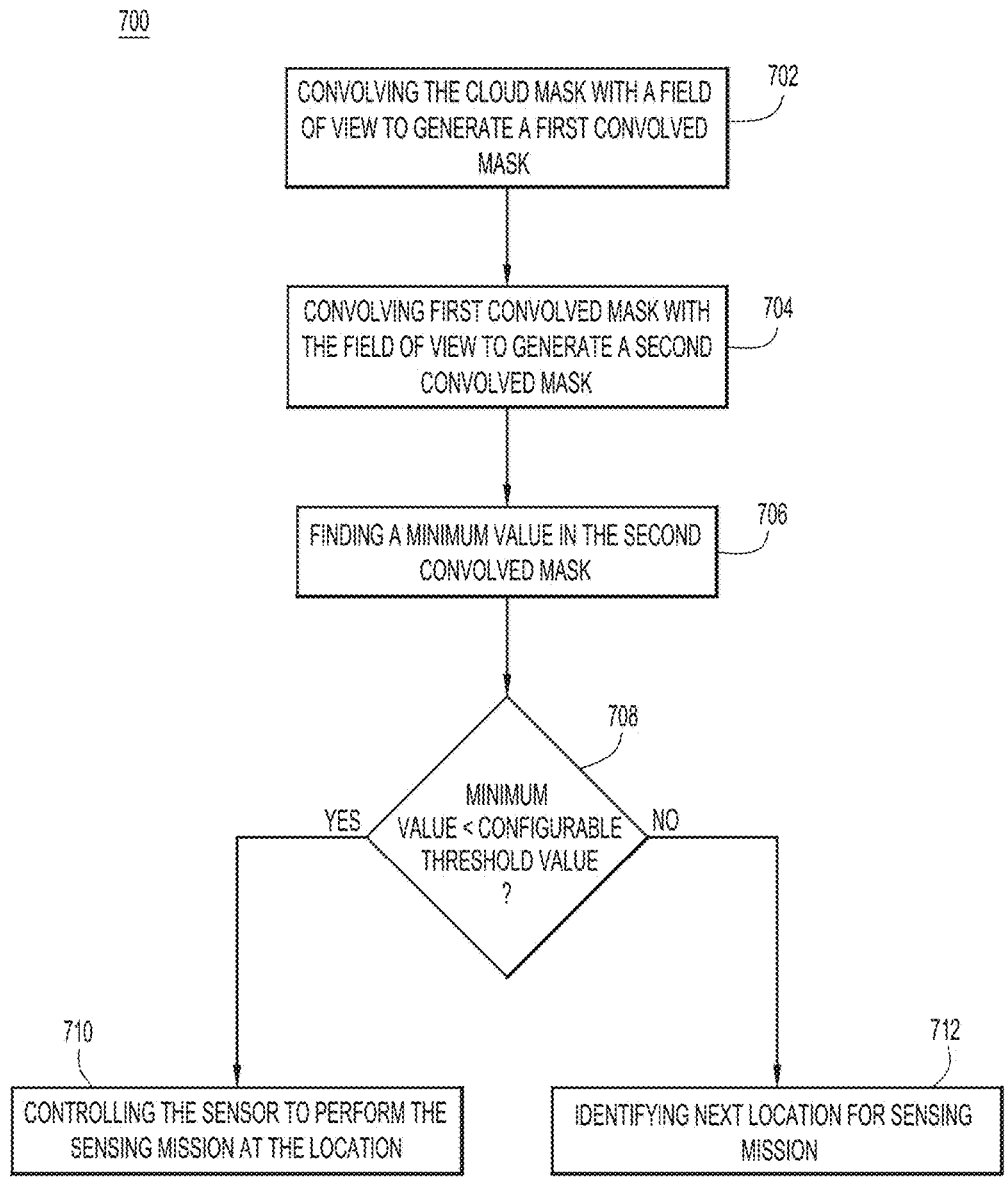
FIG. 7 is a flow chart illustrating a method for determining a measurement location from a cloud mask, according to an example embodiment.

Reference will now be made to FIG. 7. FIG. 7 is a flow chart depicting a method 700 for determining a desired measurement location substantially without cloud cover and suitable for measuring an atmospheric condition, according to an example embodiment. In particular, method 700 may be implemented as cloud-avoidance algorithm executable by a processor to locate a desired spot for a sensing mission. At 702, a processor is configured to convolve a cloud mask with a field of view of the sensor to generate a first convolved mask. For example, after an image is converted into a cloud mask by a cloud detection algorithm, the cloud mask can be convolved with an FOV mask having an FOV area of the sensor. In particular, a cloud mask may be a binary bitmap including pixels at the cloud area(s) having a value of one (white pixels) and pixels at the non-cloud area having a value of zero (black pixels). In some embodiments, pixels at the edge of the cloud mask are assigned a small value, such as 0.0001, regardless of whether they are in a non-cloud or cloud area. An example cloud mask is shown in FIG. 4C. An FOV mask includes an FOV area representing the FOV of the sensor. Pixels of the FOV mask within the FOV area are given a value of one (1) while pixels outside of the FOV area are given a value of zero (0). The convolution value from the cloud mask and the FOV mask is assigned to the pixel at the center of the FOV area. As the center of FOV on the FOV mask moves through every pixel of the cloud mask, each pixel on the cloud mask is given a convolution value so as to generate a first convolved mask.

At 704, the processor is configured to convolve first convolved mask with the sensor field of view to generate a second convolved mask. Similar to operation 702, the convolution is performed between the first convolved mask and the FOV masks. An example second convolved mask is shown in FIG. 4D.

At 706, the processor finds a minimum value in the second convolved mask such that the location having the minimum value is used as the desired location for the sensor to measure the atmospheric condition. The location having the minimum value in the second convolved mask is a desired location because it is spaced apart from a boundary of the cloud area(s) and from edges of the cloud mask.

In some embodiments, to improve the success rate of sensing, at 708 the processor is configured to determine whether the minimum value in the second convolved mask is less than a configurable threshold value. If the minimum value is less than the threshold value (Yes at 708), at 710 the processor controls the sensor to measure the atmospheric condition at the location corresponding to the minimum value. In one embodiment, the processor converts the pixel location of minimum convolution value to a pointing angle for repoint the sensor. If the minimum value is not less than the threshold value (No at 708), at 712 the processor is configured to process next image to identify next desired location for measuring the atmospheric condition. That is, if the minimum value is not less than the threshold value, the processor does not instruct the sensor to sense signals at the location corresponding to the minimum value, as the location may be covered with cloud sufficient to obstruct correct sensing of signals.

Figure 1:
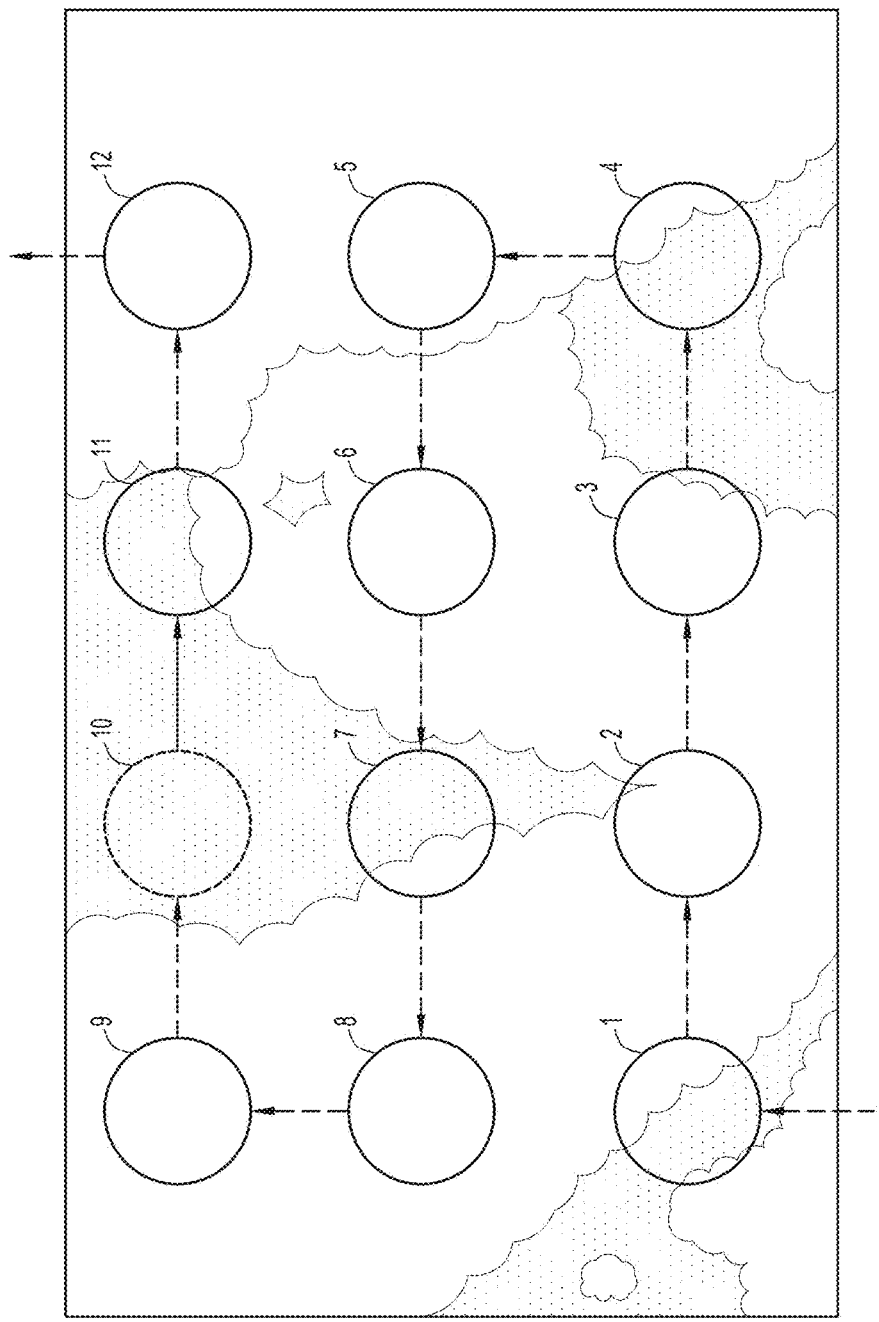
FIG. 1 is an image showing a conventional scanning method of detecting greenhouse gas concentrations.
Figure 2:
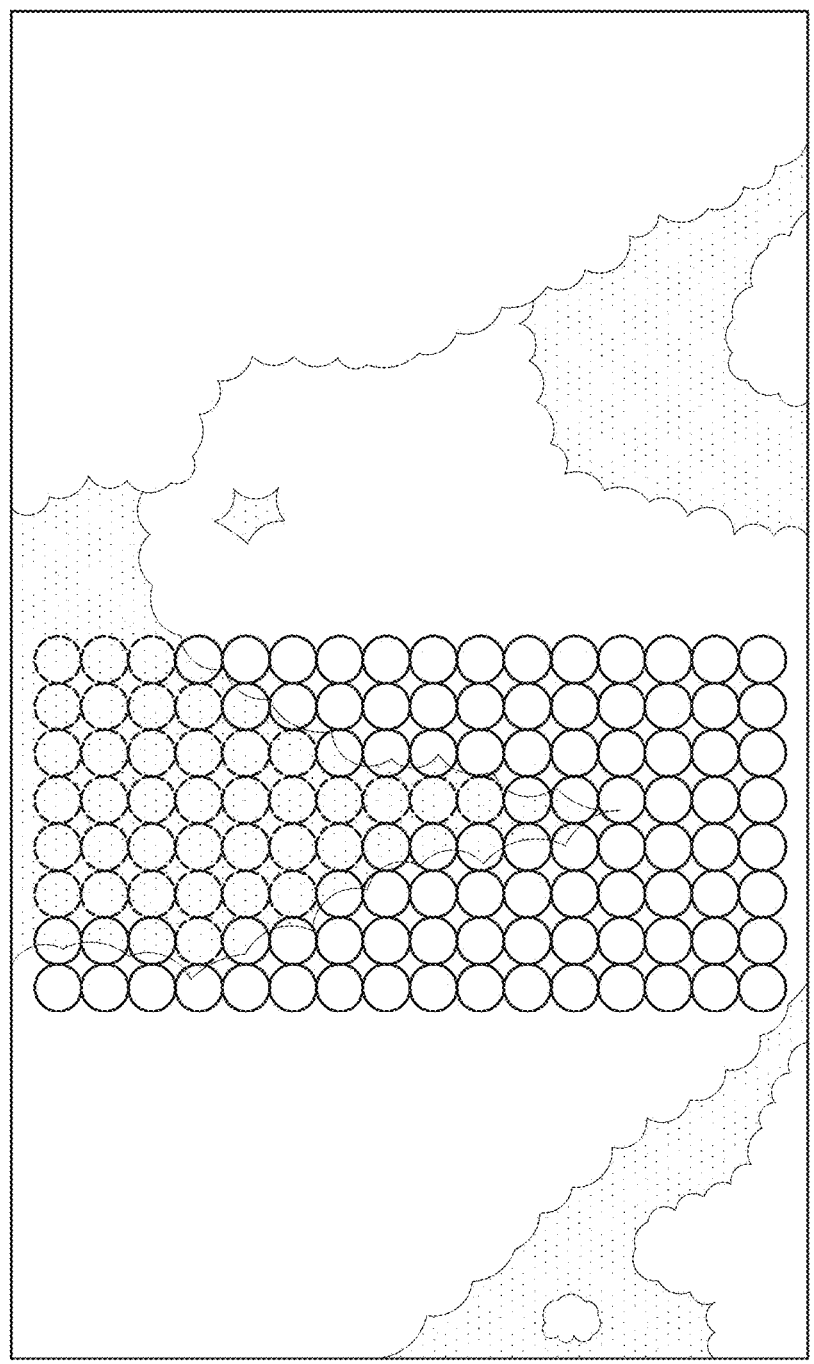
FIG. 2 is an image showing another scanning method of detecting greenhouse gas concentrations.
Figure 8:
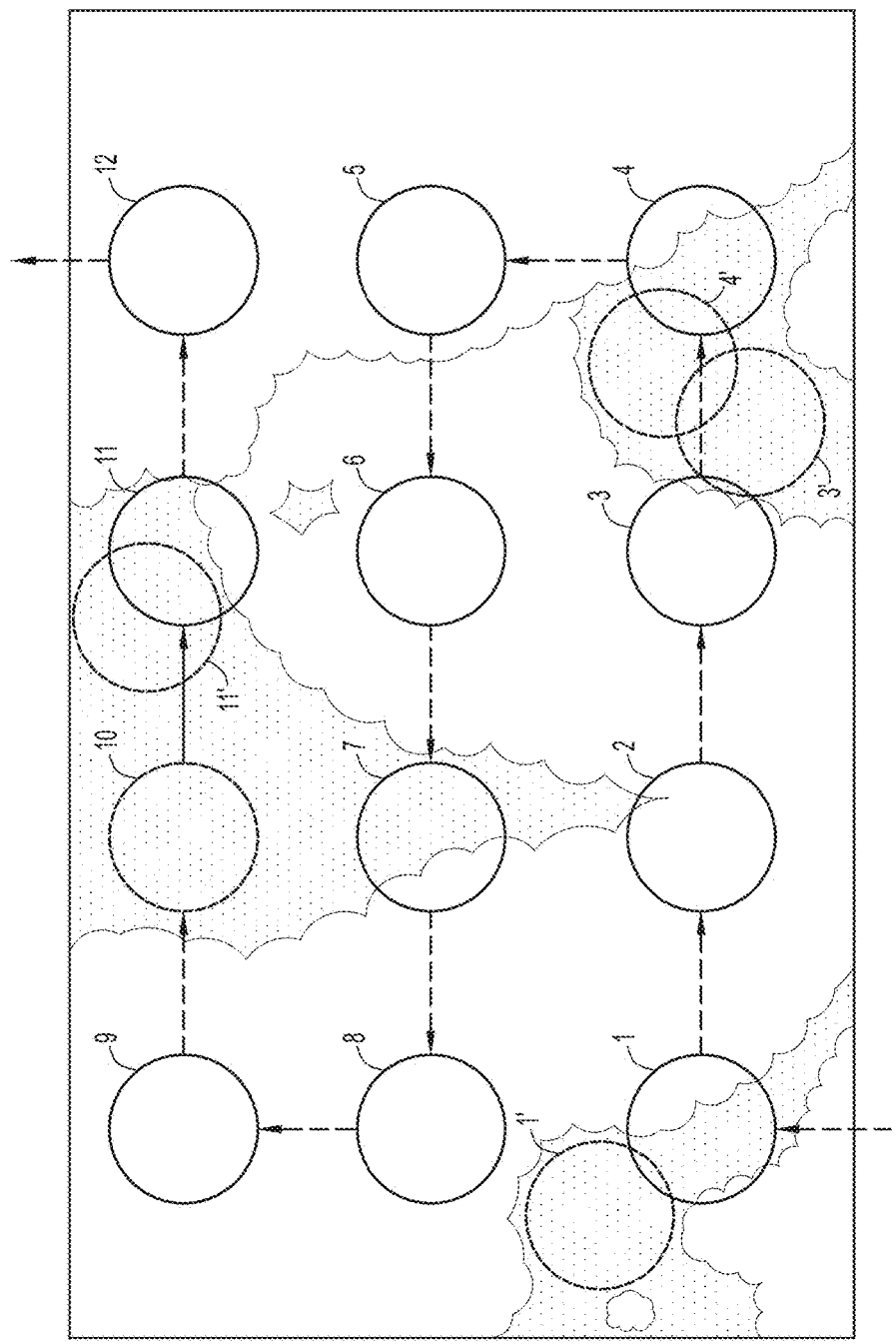
FIG. 8 is an image showing results of intelligently pointing a sensor to a measurement location and a comparison with detection results of the conventional method depicted in FIG. 1.

Techniques disclosed herein enables a sensing system to more effectively and accurately measuring atmospheric conditions. FIG. 8 shows a result of intelligently pointing a sensor to conduct a sensing mission, according to an example embodiment. In FIG. 8, locations 1-12 represent areas sensed using the conventional scanning method described with reference to FIG. 1. Out of the 12 locations, only data collected from location 10 can be used because location 10 is not cloud covered. Techniques disclosed herein point the sensor to 5 locations in FIG. 8, i.e., locations 1', 3', 4', 10, and 11', to sense signals. The data collected from those five locations are all usable for determining greenhouse gas concentrations, resulting in improved success rate of sensing. This may reduce post-collection calculation to obtain sensing results.

In a non-limiting embodiment, the techniques disclosed herein include collecting a color image using a camera, aggregating pixels in the image, applying cloud detection algorithm to create a cloud mask, finding a substantially cloud-free location, repointing a sensor to the substantially cloud-free location, conducting sensing, and repeating the above operations to conduct further sensing.

At a high-level, the techniques disclosed herein use a camera integrated within a sensor to take a color image of the desired location, use the image to find a cloud free location if it exists, and then repoint the sensor to the nearest substantially cloud-free region so that the greenhouse gases observation is taken in a non-cloud area.

In another embodiment, a mechanical mechanism including a mirror assembly is controlled to point the sensor to a desired location to make greenhouse gas observation. A camera is controlled to collect a color image, aggregate the pixels in the image, and transmit the aggregated image to a computer having a processor. The processor applies a cloud detection algorithm to create a cloud mask, from which the processor finds a substantially cloud-free location, and repoints a sensor to the measurement location where the sensor makes the greenhouse/trace gas observation.

While the invention has been illustrated and described in detail and with reference to specific embodiments thereof, it is nevertheless not intended to be limited to the details shown, since it will be apparent to one skilled in the art that various modifications and structural changes may be made therein without departing from the scope of the inventions and within the scope and range of equivalents of the claims. For example, although some embodiments described herein are described in the context of greenhouse gas concentrations, the present invention is not limited to this application. In addition, various features from one of the embodiments may be incorporated into another of the embodiments. For example, in different embodiments, any number and configuration of sensors 308 may be utilized with various embodiments. Accordingly, it is appropriate that the appended claims be construed broadly and in a manner consistent with the scope of the disclosure as set forth in the following claims.

Finally, it is intended that the present invention cover the modifications and variations of this invention that come within the scope of the appended claims and their equivalents. Further, the term "example" is used herein to describe an example or illustration. Any embodiment described herein as an example is not to be construed as a preferred or advantageous embodiment, but rather as one example or illustration of a possible embodiment of the invention.

What is claimed is:

1. A method for measuring atmospheric conditions existing below clouds from a satellite or airborne craft located above the clouds, said method comprising:
   determining a cloud-free measurement location below the satellite or aircraft by:
      at a computing device on the satellite or aircraft, receiving from a downward-looking imager, image data representing an image of an atmospheric region below the imager;
      creating a cloud mask from the image data, the cloud mask comprising a grid of plural sequential image area sections representing respective plural locations sequentially scanned by said imager;
      sensing which of said image area sections are cloud-free, which of said image area sections include clouds, and which of said image area sections include a cloud boundary;

selecting as the measurement location at least one cloud-free image area section that is spaced in said mask apart from the cloud boundary image area sections and from edges of the cloud mask;

steering a line of sight of a sensor to correspond to the measurement location; and measuring an atmospheric condition with the sensor at the measurement location within the cloud-free area.

2. The method of claim 1, wherein the image data includes pixels, and the method further comprises:

aggregating groups of adjacent pixels to form said area sections as aggregated pixels so as to generate an aggregated image from the image.

3. The method of claim 1, wherein the image data includes data of red (R), green (G), and blue (B) pixels, and creating the cloud mask comprises:

converting RGB pixel data of the image data into hue (H), saturation (S), and value (V) data; and determining that a pixel is in a cloud area section if an S value of the pixel is greater than a first threshold and a V value of the pixel is less than a second threshold.

4. The method of claim 1, wherein the image data includes data of red (R), green (G), and blue (B) pixels, and creating the cloud mask comprises:

determining that a pixel is in a cloud area section if an absolute value of a difference between an R value and a G value of the pixel is less than or equal to a first threshold and a difference between a B value and an average of the R value and the G value is greater than a second threshold.

5. The method of claim 1, wherein the image data includes data of red (R), green (G), and blue (B) pixels, and creating the cloud mask comprises:

determining a minimum of an R value, a G value, and a B value of a pixel;

determining that the pixel is a cloud area section if the minimum is greater than a first threshold; or determining that the pixel is in a cloud-free area section if the minimum is less than a second threshold.

6. The method of claim 1, wherein determining the measurement location comprises:

convolving the cloud mask with a sensor field of view to generate a first convolved mask; and convolving the first convolved mask with the sensor field of view to generate a second convolved mask.

7. The method of claim 6, wherein the measurement location is determined by finding a minimum value in the second convolved mask.

8. The method of claim 7, wherein measuring the atmospheric condition with the sensor at the measurement location is performed in response to the minimum value being less than a configurable threshold value.

9. A system for measuring atmospheric conditions existing below clouds from a satellite or aircraft located above the clouds, said system comprising:

a sensor configured to measure an atmospheric condition;

a steering mechanism to point the sensor along a line of sight to measure the atmospheric condition;

a downward-looking imager configured to take images of an atmospheric region below the imager;

a processor; and a memory to store data and instructions executable by the processor;

wherein the processor is configured to execute the instructions to:

receive, from the imager, image data representing an image of aft said atmospheric region;

create a cloud mask from the image data, the cloud mask comprising a grid of plural sequential image area sections representing respective plural locations sequentially scanned by said imager;

sense which of said image area sections are cloud-free area sections, which of said image area sections include clouds, and which of said image area sections include cloud boundaries;

select as the measurement location at least one cloud-free image area section that is spaced in said cloud mask apart from cloud boundary image area sections and from edges of the cloud mask; and instruct the steering mechanism to point the sensor to a line of sight corresponding to the measurement location to allow the sensor to measure the atmospheric condition at the measurement location.

10. The system of claim 9, wherein the image data includes data of red (R), green (G), and blue (B) pixels, and the processor is configured to execute the instructions to:

convert RGB pixel data of the image data into hue (H), saturation (S), and value (V) data; and determine that a pixel is in a cloud area section if an S value of the pixel is greater than a first threshold and a V value of the pixel is less than a second threshold.

11. The system of claim 9, wherein the image data includes data of red (R), green (G), and blue (B) pixels, and the processor is configured to execute the instructions to:

determine that a pixel is in a cloud area section if an absolute value of a difference between an R value and a G value of the second pixel is less than or equal to a first threshold and a difference between a B value and an average of the R value and the G value is greater than a second threshold.

12. The system of claim 9, wherein the image data includes data of red (R), green (G), and blue (B) pixels, and the processor is configured to execute the instructions to:

determine a minimum of an R value, a G value, and a B value of a pixel;

determine that the pixel is in a cloud area section if the minimum is greater than a first threshold; or determine that the pixel is in a cloud-free area section if the minimum is less than a second threshold.

13. The system of claim 9, wherein the processor is configured to execute the instructions to:

convolve the cloud mask with a sensor field of view to generate a first convolved mask;

convolve the first convolved mask with the sensor field of view to generate a second convolved mask; and determine the measurement location as a point in the second convolved mask that has a minimum value.

14. The system of claim 13, wherein the processor is configured to execute the instructions to:

control the sensor to measure the atmospheric condition at the measurement location in response to the minimum value being less than a configurable threshold value.

15. A non-transitory computer-readable storage medium encoded with software comprising computer executable instructions which, when executed by a processor, cause the processor to:

receive, from an imager located above clouds, image data representing an image of an atmospheric region below the imager;

create a cloud mask from the image data, the cloud mask comprising a grid of plural sequential image area sections representing respective plural locations sequentially scanned by said imager;

sense which of said image area sections are cloud-free, which of said image area sections include clouds and which of said image area sections include cloud boundaries;

select as a measurement location at least one cloud-free image area section that is spaced in said mask apart from cloud boundary image area section and from edges of the mask; and instruct a steering system to point a sensor to a line of sight corresponding to the measurement location to allow the sensor to measure an atmospheric condition at the measurement location.

16. The non-transitory computer-readable storage medium of claim 15, wherein the image data includes data of red (R), green (G), and blue (B) pixels, and the instructions cause the processor to:

convert RGB pixel data of the image data into hue (H), saturation (S), and value (V) data; and determine that a pixel is in a cloud area section if an S value of the pixel is greater than a first threshold and a V value of the pixel is less than a second threshold.

17. The non-transitory computer-readable storage medium of claim 15, wherein the image data includes data of red (R), green (G), and blue (B) pixels, and the instructions cause the processor to:

determine that a pixel is in a cloud area section if an absolute value of a difference between an R value and a G value of the pixel is less than or equal to a first threshold and a difference between a B value and an average of the R value and the G value is greater than a second threshold.

18. The non-transitory computer-readable storage medium of claim 15, wherein the image data includes data of red (R), green (G), and blue (B) pixels, and the instructions cause the processor to:

determine a minimum of an R value, a G value, and a B value of a pixel;

determine that the pixel is in a cloud area section if the minimum is greater than a first threshold; or determine that the pixel is in a cloud-free area section if the minimum is less than a second threshold.

19. The non-transitory computer-readable storage medium of claim 15, wherein the instructions cause the processor to:

convolve the cloud mask with a sensor field of view to generate a first convolved mask;

convolve first convolved mask with the sensor field of view to generate a second convolved mask; and determine the measurement location as a point in the second convolved mask that has a minimum value.

20. The non-transitory computer-readable storage medium of claim 19, wherein the instructions cause the processor to:

control the sensor to measure the atmospheric condition at the measurement location in response to the minimum value being less than a configurable threshold value.

* * * * *